United States Patent
Esko et al.

(10) Patent No.: US 9,757,468 B2
(45) Date of Patent: Sep. 12, 2017

(54) INTRANASAL ADMINISTRATION OF GUANIDINYLATED AMINOGLYCOSIDES

(71) Applicant: The Regents of the University of California, La Jolla, CA (US)

(72) Inventors: Jeffrey D. Esko, San Diego, CA (US); Yitzhak Tor, San Diego, CA (US); Wenyong Tong, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/774,257

(22) PCT Filed: Mar. 13, 2014

(86) PCT No.: PCT/US2014/025382
§ 371 (c)(1),
(2) Date: Sep. 10, 2015

(87) PCT Pub. No.: WO2014/159878
PCT Pub. Date: Oct. 2, 2014

(65) Prior Publication Data
US 2016/0015822 A1    Jan. 21, 2016

Related U.S. Application Data

(60) Provisional application No. 61/779,383, filed on Mar. 13, 2013, provisional application No. 61/803,961, filed on Mar. 21, 2013.

(51) Int. Cl.
| | |
|---|---|
| A61K 38/46 | (2006.01) |
| A61K 47/48 | (2006.01) |
| A61K 9/00 | (2006.01) |
| A61K 38/47 | (2006.01) |
| A61K 39/395 | (2006.01) |

(52) U.S. Cl.
CPC ...... *A61K 47/48092* (2013.01); *A61K 9/0043* (2013.01); *A61K 38/46* (2013.01); *A61K 38/47* (2013.01); *A61K 39/39533* (2013.01); *A61K 47/48115* (2013.01); *C12Y 302/01076* (2013.01); *C12Y 310/01001* (2013.01)

(58) Field of Classification Search
None
See application file for complete search history.

(56) References Cited

U.S. PATENT DOCUMENTS

| | | |
|---|---|---|
| 6,468,798 B1 | 10/2002 | Debs et al. |
| 6,471,996 B1 | 10/2002 | Sokoll et al. |
| 6,472,375 B1 | 10/2002 | Hoon et al. |
| 8,071,535 B2 | 12/2011 | Tor et al. |
| 2008/0305077 A1 | 12/2008 | Frey, II et al. |
| 2009/0047234 A1 | 2/2009 | Touitou et al. |
| 2012/0189601 A1 | 7/2012 | Esko et al. |

FOREIGN PATENT DOCUMENTS

| | | |
|---|---|---|
| WO | WO 2005/025513 | 3/2005 |
| WO | WO 2008/049897 | 5/2008 |
| WO | WO 2011/034951 | 3/2011 |

OTHER PUBLICATIONS

Türker, S; Onur, E; Ozer, Y "Nasal route and drug delivery systems." Pharm World Sci. Jun. 2004, 26(3), pp. 137-142.*
Thermo Fisher Scientific "Comparison of Antibody IgG Binding Proteins", Thermo Fisher Scientific, 2016, 2 pages.*
Berge et al., "Pharmaceutical Salts," J Pharm Sci., 1977, 66(1):1-19.
Hamajima et al., "Intranasal administration of HIV-DNA vaccine formulated with a polymer, carboxymethylcellulose, augments mucosal antibody production and cell-mediated immune response," Clin Immunol Immunopathol. Aug. 1998;88(2):205-10.
Pavan et al. "Progress in Drug Delivery to the Central Nervous System by the Prodrug Approach" Molecules. May 1, 2008;13(5):1035-65.
Wolf et al, "Lysosomal enzyme can bypass the blood-brain barrier and reach the CNS following intranasal administration," Mol Genet Metab. May 2012;106(1):131-4. doi:10.1016/j.ymgme.2012.02.006. Epub Feb. 10, 2012.
International Search Report and Written Opinion in International Application No. PCT/US2014/025382, mailed on Oct. 23, 2014, 7 pages.
International Preliminary Report on Patentability in International Application No. PCT/US2014/025382, mailed on Sep. 24, 2015, 6 pages.

* cited by examiner

*Primary Examiner* — Chris R Tate
*Assistant Examiner* — Aaron J Kosar
(74) *Attorney, Agent, or Firm* — Fish & Richardson P.C.

(57) ABSTRACT

This disclosure relates to intranasal administration of conjugates comprising guanidinylated aminoglycosides ("guanidinoglycosides") and a polypeptide (e.g., an enzyme, antibody, or polypeptide growth factor). For example, such administration methods are useful for delivering a polypeptide to the brain and/or cerebrospinal fluid. Such methods are useful for treating a lysosomal storage disease through intranasal administration of a conjugate comprising one or more guanidinoglycosides and an enzyme useful for treating a lysosomal storage disease.

15 Claims, 5 Drawing Sheets

OB=Olfactory Bulb  CTX= Cerebral Cortex  CB= Cerebellum

INTRANASAL ADMINISTRATION OF GUANIDINYLATED AMINOGLYCOSIDES

CROSS-REFERENCE TO RELATED APPLICATIONS

This application is a National Stage application under 35 U.S.C. §371 of International Application No. PCT/US2014/025382, having an International Filing Date of Mar. 13, 2014, which claims priority to U.S. Provisional Application Ser. No. 61/779,383, filed Mar. 13, 2013, and 61/803,961, filed Mar. 21, 2013, each of which are incorporated by reference in their entireties.

FEDERALLY SPONSORED RESEARCH OR DEVELOPMENT

This invention was made with Government support under Grant Nos. GM077471 and GM33063 awarded by the National Institutes of Health. The Government has certain rights in the invention.

TECHNICAL FIELD

This disclosure relates to intranasal administration of conjugates comprising guanidinylated aminoglycosides ("guanidinoglycosides") and a polypeptide (e.g., a growth factor, an enzyme, or an antibody). For example, such administration methods are useful for delivering a polypeptide to the brain and/or cerebrospinal fluid. Such methods are useful for treating a lysosomal storage disease through intranasal administration of a conjugate comprising one or more guanidinoglycosides and an enzyme useful for treating a lysosomal storage disease. Other uses include, but are not limited to, delivery of a therapeutic antibody or neurotrophic factors to treat cancer or neurodegenerative disorders, respectively.

BACKGROUND

Greater than 98% of small molecule and nearly 100% of large molecule CNS drugs do not cross the BBB effectively. Intracerebroventricular or intraparenchymal administration can directly deliver therapeutics to the brain and/or cerebrospinal fluid; however, these methods are invasive, inconvenient, and impractical for the numbers of individuals requiring therapeutic interventions for treating CNS disorders. Intranasal administration of therapeutic compounds or polypeptides may, in some cases, increase the effectiveness of certain therapeutic compounds or polypeptides in bypassing the blood brain barrier (BBB) and delivering the compound or polypeptide directly to the CNS (e.g., brain and cerebrospinal fluid). Thus, intranasal administration of therapeutic compounds or polypeptides may allow increased prevention and/or treatment of certain diseases or conditions. Intranasal administration is a non-invasive and convenient means to rapidly target therapeutics of varying physical and chemical properties to the CNS.

The intranasal method of administration holds great promise as an alternative to more invasive routes; however, a number of factors limit the efficiency of intranasal administration to the CNS. Absorption of intranasally applied drugs into the capillary network in the nasal mucosa can decrease the amount of therapeutic available for direct transport into the CNS. Additional factors within the nasal cavity, including the presence of nasal mucociliary clearance mechanisms, metabolizing enzymes, efflux transporters and nasal congestion can also reduce the efficiency of delivery into the CNS. For example, therapeutic compounds or polypeptides may be absorbed into the blood and/or delivered to peripheral (non-target) tissues, thus reducing delivery of the compound to the CNS.

SUMMARY

The present disclosure provides guanidinoglycoside-containing conjugates, which exhibit enhanced delivery to the central nervous system (CNS) when administered via intranasal routes. Such conjugates are useful in the delivery of therapeutic compounds for a number of diseases and disorders including, but not limited to, lysosomal storage disorders, cancer and neurological disorders. Prior work suggests that uptake into the brain and/or cerebrospinal fluid by intranasal administration may be limited to low molecular weight compounds and relatively short polypeptides. One of the largest therapeutic proteins reported to be delivered to the brain and/or cerebrospinal fluid via intranasal administration in animals is nerve growth factor (27,500 Daltons). The present disclosure demonstrates effective administration of larger polypeptides, for example, α-iduronidase, which has a mass 72,000 Daltons and immunoglobulin G, which has a mass of ~150,000 Daltons. In addition, while the level of delivery to the brain and/or cerebrospinal fluid of unmodified biologics is typically very low, intranasal delivery of a conjugate as provided herein has been shown to be comparably efficient.

Provided herein is a method for treating a lysosomal storage disease in a patient, the method comprising intranasal administration of a therapeutically effective amount of a conjugate comprising one or more guanidinoglycosides and an enzyme useful for treating a lysosomal storage disease to the patient.

In some embodiments, the guanidinoglycoside is covalently bound to the enzyme, wherein the covalent bond is direct or optionally through a linker. For example, the conjugate can be conjugated through a functional group attached to the guanidinoglycoside. Functional groups can include, but are not limited to, thiol, N-hydroxysuccinimide, and amide. The functional group can be attached to various linkers which are well known in the art.

Guanidinoglycosides are derived from natural and synthetic aminoglycosides. In some embodiments, the one or more guanidinoglycosides are derived from an aminoglycoside antibiotic. For example, the guanidinoglycoside is selected from the group consisting of guanidino-amikacin, guanidino-gentamicin, guanidino-kanamycin, guanidino-neomycin (GNeo), guanidino-netilmicin, guanidino-O-2,6-diamino-2,6-dideoxy-beta-L-idopyranosyl (1→3)-O-beta-D-ribofuranosyl (1→5)-O-[2-amino-2-deoxy-alpha-D-glucopyranosyl-(1→4)]-2-deoxystreptamine, guanidino-paramycin, guanidino-streptomycin, guanidino-paromomycin, guanidine-dibekacin, guanidine-arbekacin, guanidino-isepamicin, guanidino-sisomicin, guanidine-ribostamycin, and guanidino-tobramycin.

In some embodiments, the enzyme can be selected from the group consisting of: α-D-mannosidase; N-aspartyl-β-glucosaminidase; acid lipase; hexosaminidase A; α-galactosidase A; β-galactosidase; ceramidase; fucosidase; β-glucosidase; N-acetylglucosamine-1-phosphotransferase; galactocerebrosidase; arylsulfatase A; N-acetylglucosamine-1-phosphotransferase; α-L-iduronidase; iduronate 2-sulfatase; heparan sulfamidase; N-acetylglucosaminidase; acetyl-CoA:α-glucosaminide acetyltransferase; N-acetylglucosamine 6-sulfatase; N-acetylgalactosamine-6-sulfate sulfatase; N-acetylgalactosamine-4-sulfatase; β-glucuronidase; hyaluronidase; sialidase; other sulfatases; sphingomyelinase; acid α-glucosidase; β-mannosidase; cathepsin K; β-hexosaminidase A; β-hexosaminidase B; α-N-acetylgalactosaminidase; sialin; and hexosaminidase A. For example, the enzyme can be β-glucuronidase, heparan sulfamidase or α-iduronidase.

In some embodiments, the lysosomal storage disease is selected from the group consisting of: Sulfatase Activator Deficiency; Alpha-mannosidosis; Aspartylglucosaminuria; Cholesteryl ester storage disease; Chronic Hexosaminidase A Deficiency; Cystinosis; Danon disease; Fabry disease; Farber disease; Fucosidosis; Galactosialidosis; Gaucher disease; GM1 gangliosidosis; I-Cell disease; Infantile Free Sialic Acid Storage Disease; Juvenile hexosaminidase A deficiency; Krabbe disease; Metachromatic Leukodystrophy; mucopolysaccharidoses disorders; multiple sulfatase deficiency; Niemann-Pick disease; Neuronal Ceroid Lipofuscinoses; Pompe disease; Pycnodysostosis; Sandhoff disease; Schindler disease; Salla disease; Tay-Sachs; and Wolman disease.

Non-limiting examples of mucopolysaccharidoses disorders include Pseudo-Hurler polydystrophy; Hurler Syndrome; Scheie syndrome; Hurler-Scheie syndrome; Hunter syndrome; Sanfilippo syndrome type A; Sanfilippo syndrome type B; Sanfilippo syndrome type C; Sanfilippo syndrome type D; Sanfilippo syndrome type E, Morquio type A; Morquio type B; Maroteaux-Lamy; Sly syndrome; and Natowicz syndrome Hyaluronidase deficiency.

A Neuronal Ceroid Lipofuscinoses can include, for example, CLN6 disease; Batten-Spielmeyer-Vogt/Juvenile NCL/CLN3 disease; Finnish Variant/Late Infantile CLN5; Jansky-Bielschowsky disease/Late infantile CLN2/TPP1 Disease; Kufs/Adult-onset NCL/CLN4 disease; Northern Epilepsy/variant Late Infantile CLN8; Santavuori-Haltia/Infantile CLN1/PPT disease; and β-mannosidosis.

Also provided herein is a method for increasing the cellular uptake of an enzyme useful for treating a lysosomal storage disease in a patient, the method comprising: a) coupling the enzyme to one or more guanidinoglycosides to form a conjugate; and b) administering the conjugate to the patient via intranasal administration.

Further provided herein is a method for treating a CNS disorder in a patient, the method comprising administering to the patient via intranasal administration a therapeutically effective amount of a conjugate comprising one or more guanidinoglycosides and a therapeutically active compound or polypeptide useful for treating the CNS disorder.

In some embodiments, the therapeutically active polypeptide can be a growth factor selected from the group consisting of neurotrophins (e.g., NGF, BDNF, neurexins), tissue growth factors (e.g., FGFs, Wnts, BMPs). In other embodiments, the therapeutic polypeptide can be a monoclonal antibody or a purified immunoglobulin fraction directed against a particular antigen present on tumor cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Definitions

Figure 1:
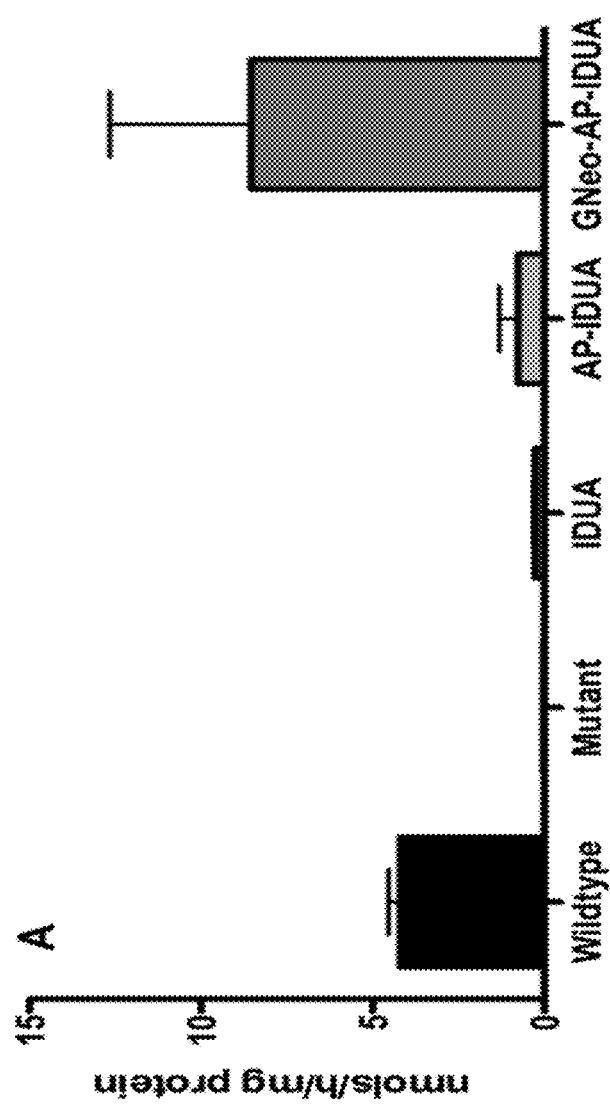
FIG. 1 is a bar graph showing the activity of α-iduronidase in the brain of mice following intranasal administration of various formulations of α-iduronidase.

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "therapeutically effective amount" of a conjugate with respect to the subject method of treatment, refers to an amount of the conjugate(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Conjugates and Methods of Treatment

The present disclosure provides guanidinoglycoside-containing conjugates, which exhibit enhanced uptake when administered via intranasal administration. Such conjugates are useful in the delivery of therapeutic compounds for a number of diseases and disorders including, but not limited to, lysosomal storage disorders, brain tumors, and central nervous system (CNS) or neurological disorders. Prior work suggests that uptake into the brain by intranasal administration may be limited to low molecular weight compounds and polypeptides. One of the largest therapeutic proteins reported to be delivered to the brain via intranasal administration in animals is nerve growth factor (27,500 Daltons).

The present disclosure demonstrates effective administration of larger polypeptides, for example, α-iduronidase, which has a mass 72,000 Daltons and immunoglobulin G, which has a mass of ~150,000 Daltons. In addition, while the level of delivery to the brain of unmodified biologics is typically very low, intranasal delivery of a conjugate as provided herein has been shown to be comparably efficient. For example, Wolf et al. (2012 *Molec. Genetics and Metabolism* 106: 131), describe intranasal delivery of concentrated (naked) ALDURAZYME® (laronidase) and of α-L-iduronidase (IDUA) expressed in an AAV vector and subsequently detected the enzyme's activity throughout the brain. The levels of expression, however, were extremely low. As described herein, the covalent conjugation of guanidinylated neomycin to ALDURAZYME led to significant delivery to the brain.

Conjugates include one or more guanidinoglycosides conjugated to one or more therapeutic agents or polypeptides (e.g., enzymes, growth factors, or antibodies). The conjugates provided herein are described, for example, in U.S. Pat. No. 8,071,535 and U.S. Patent Publication No. U.S. 2012/0189601, both of which are incorporated by reference in their entirety.

In particular, the present disclosure provides compositions and methods for treating lysosomal storage disorders through assisted enzyme replacement therapy. Genetic diseases that result in the absence of essential enzymes (or the presence or defective enzymes) can, in certain cases, be treated by intravenous infusion of the missing protein. Large quantities of enzymes are typically administered with varying level of success. The present disclosure provides new methods of administration for delivery of vehicles that upon conjugation to the missing enzymes, facilitate their transport and restore in vivo activity at high efficiency.

The delivery vehicle or carrier comprises covalently conjugating guanidinylated neomycin (guanidinoneomycin; GNeo) or other guanidinylated glycosides to a therapeutically active compound or polypeptide (e.g., an enzyme or antibody), wherein the carrier transports the therapeutically active compound or polypeptide either across tissues or into the interior of the cell by way of proteoglycans (e.g., heparan sulfate proteoglycans) in the extracellular matrix and on the cell surface. Most therapeutic compounds or polypeptides, however, do not bind to heparan sulfate proteoglycans. This system has a very high capacity since proteoglycans are much more abundant on cells and in the extracellular matrix than other kinds of receptors. For example, conjugating a therapeutic compound or polypeptide to a guanidinoglycoside as provided herein can facilitate binding of the conjugate to a proteoglycan on the nasal epithelium, which can, in turn, facilitate rapid transport of the conjugate into the brain and/or cerebrospinal fluid.

Evidence indicates that the new guanidinylated glycosides act as transporters by binding to cell surface proteoglycan receptors. These receptors are numerous and undergo continuous endocytosis. Thus, therapeutic compounds or polypeptides conjugated to a guanidinylated glycoside ("cargo") take advantage of the binding of the guanidinylated glycoside to the proteoglycans and "piggy-back" into the cell. In the case of enzymes for treating lysosomal storage disorders, during this process some of the cargo (e.g., enzyme or other therapeutic compound) appears in the cytoplasm, some goes to the lysosome, and some may go to other parts of the cell. The precise mechanism for routing the cargo has not been established, but the net result is the appearance of cargo in desirable subcompartments of the cell. Furthermore, the method is highly selective for proteoglycan receptors on the cell, which provides a single portal of entry. High activity at low concentrations suggests minimal adverse effects. Additionally, conjugation facilitates delivery across the nasal epithelium into the CNS.

Clinical applications include enzyme replacement therapy for disorders in which a cell is missing an enzyme or polypeptide. Specific examples include lysosomal storage diseases, congenital disorders of glycosylation, and metabolic disorders characterized by missing or reduced enzyme activity in the cytoplasm. Non-limiting examples of lysosomal storage diseases include: Activator Deficiency; Alpha-mannosidosis; Aspartylglucosaminuria; Cholesteryl ester storage disease; Chronic Hexosaminidase A Deficiency; Cystinosis; Danon disease; Fabry disease; Farber disease; Fucosidosis; Galactosialidosis; Gaucher disease; GM1 gangliosidosis; I-Cell disease; Infantile Free Sialic Acid Storage Disease; Juvenile Hexosaminidase A deficiency; Krabbe disease; Metachromatic Leukodystrophy; Mucopolysaccharidoses disorders (e.g., Pseudo-Hurler polydystrophy; Hurler Syndrome; Scheie syndrome; Hurler-Scheie syndrome; Hunter syndrome; Sanfilippo syndrome type A; Sanfilippo syndrome type B; Sanfilippo syndrome type C; Sanfilippo syndrome type D; Morquio type A; Morquio type B; Maroteaux-Lamy; Sly syndrome; and Natowicz syndrome Hyaluronidase deficiency); Multiple sulfatase deficiency; Niemann-Pick disease; Neuronal Ceroid Lipofuscinoses (e.g, CLN6 disease; Batten-Spielmeyer-Vogt/Juvenile NCL/CLN3 disease; Finnish Variant/Late Infantile CLN5; Jansky-Bielschowsky disease/Late infantile CLN2/TPP1 Disease; Kufs/Adult-onset NCL/CLN4 disease; Northern Epilepsy/variant Late Infantile CLN8; Santavuori-Haltia/Infantile CLN1/PPT disease; and β-mannosidosis); Pompe disease; Pycnodysostosis; Sandhoff disease; Schindler disease; Salla disease; Tay-Sachs; and Wolman disease.

Pharmaceutical applications include treatment of metabolic disorders in which enzymes or structural polypeptides are missing. For example, a conjugate can include one or more guanidinoglycosides and an enzyme useful in the treatment of a lysosomal storage disease. In some cases, these enzymes can include: α-D-mannosidase; N-aspartyl-β-glucosaminidase; acid lipase; hexosaminidase A; α-galactosidase A; β-galactosidase; ceramidase; fucosidase; β-glucosidase; N-acetylglucosamine-1-phosphotransferase; galactocerebrosidase; arylsulfatase A; N-acetylglucosamine-1-phosphotransferase; α-L-iduronidase; iduronate sulfatase; heparan sulfamidase; N-acetylglucosaminidase; acetyl-CoA:α-glucosaminide acetyltransferase; N-acetylglucosamine 6-sulfatase; N-acetylgalactosamine-6-sulfate sulfatase; N-acetylgalactosamine-4-sulfatase; β-glucuronidase; hyaluronidase; sialidase; sulfatase; sphingomyelinase; acid α-glucosidase; β-mannosidase; cathepsin K; β-hexosaminidase A; β-hexosaminidase B; α-N-acetylgalactosaminidase; sialin; and hexosaminidase A. In some embodiments, the enzyme is β-glucosidase or α-iduronidase. Further examples can be found, for example, in *The Metabolic and Molecular Bases of Inherited Disease* by Scriver, Beudet, Valle, Sly, Childs, Kinzler, and Vogelstein, Vol 3, part 16, chapters 134-154. Additional enzymes can include chondroitinase, heparinases, and hyaluronidase.

A polypeptide as provided herein can also include an antibody, such as a monoclonal antibody or an immunoglobulin fraction containing multiple antibodies directed to an antigen. In some embodiments, the antibodies (or a fragment thereof) can be useful in the treatment of a CNS or neurological disorder. Exemplary monoclonal antibodies include 3F8, 8H9, aducanumab, bapineuzumab, briakinumab, crenezumab, gantenerumab, ibalizumab, nimotuzumab, ozanezumab, pateclizumab, ponezumab, priliximab, pritumumab, PRO 140, ustekinumab, zalutumumab, gemtuzumab, alemtuzumab, rituximab, trastuzumab, nimtuzumab, cetuximab, bevacizumab, brentuximab vedotin, cetuximab, denusumab, gentuzumab, ibrutumomab tiuxetan, ipilimumab, ofatumumab, panitumumab, tositumomab, and trastuzumab.

A polypeptide as provided herein can further include a growth factor. In some embodiments, the therapeutically active polypeptide can be a growth factor selected from the group consisting of neurotrophins and tissue growth factors. These factors include but are not limited to EGF, NGF, BDNF, PDGF, FGF, HGF, members of the TNF family, CTGF, IGF, L1, N-CAMs (NR-CAM, NG-CAM) pleiotrophin and midkine Other proteins include contactin(s) and insulin.

In addition, intranasal administration of a conjugate provided herein can be used to treat one or more CNS or neurological disorders such as Alzheimer's disease, Parkinson's disease, amyotrophic lateral sclerosis, Friedreich's ataxia, Huntington's disease, Lewy body disease, cerebrovascular disorders, frontotemporal dementia, personality disorders, cognition disorders, motor dysfunction, eating disorders, sleep disorders, affective disorders, anxiety disorders, schizophrenia, brain tumors, ataxia, bovine spongiform encephalopathy, West Nile virus encephalitis, Neuro-AIDS, brain injury, spinal cord injury, and multiple sclerosis.

The term "guanidinoglycoside" (GG) as used herein refers to derivatives of aminoglycosides in which one or more of the ammonium groups have been converted into guanidinium groups. In some cases, all of the ammonium groups can be converted into guanidinium groups. For example, guanidinylated neomycin (guanidinoneomycin; GNeo) contains six positively charged guanidinium groups in place of the naturally occurring amino groups on the three monosaccharide units and the one cyclitol that make up the antibiotic.

Guanidinoglycosides are derived from natural and synthetic aminoglycosides. In some embodiments, the one or more guanidinoglycosides are derived from an aminoglycoside antibiotic. For example, the guanidinoglycoside is selected from the group consisting of guanidino-amikacin, guanidino-gentamicin, guanidino-kanamycin, guanidino-neomycin (GNeo), guanidino-netilmicin, guanidino-O-2,6-diamino-2,6-dideoxy-beta-L-idopyranosyl (1→3)-O-beta-D-ribofuranosyl-(1→5)-O-[2-amino-2-deoxy-alpha-D-glucopyranosyl-(1→4)]-2-deoxystreptamine, guanidino-paramycin, guanidino-streptomycin, guanidino-paromomycin, guanidine-dibekacin, guanidine-arbekacin, guanidino-isepamicin, guanidino-sisomicin, guanidine-ribostamycin, and guanidino-tobramycin.

The term "coupled" as used herein includes both covalent and noncovalent bonding of two or more moieties. In some cases, the term coupled can include covalent or noncovalent bonding, which occurs directly between the moieties or optionally via one or more linkers. A linker can be any physiologically compatible chemical group that does not interfere with the functions of the guanidinoglycoside or the polypeptide (e.g., an enzyme). Preferred linkers are synthetically easy to incorporate into the conjugates. They are also not so unduly large as to manifest an undesired biological function or targeting influence onto the conjugate. For example, a linker can include a hydrocarbon moiety, a polyethylene glycol (PEG) moiety, an oligoamide moiety, an oligoester, as well as functionalized and (chemically and enzymatic) cleavable moieties. In some embodiments, the linker can include a hydroxysuccinimide moiety or an alkaline phosphatase moiety.

In addition to the formulations and methods provided herein, methods of treating the disorders recited herein can be combined with existing methods for treating these conditions. For example, in the case of cancer, the formulations can be combined with, chemotherapy, irradiation, and/or surgery.

Pharmaceutical Compositions and Administration

The methods provided herein include the manufacture and use of pharmaceutical compositions suitable for conjugate intranasal administration, which include one or more of the conjugates provided herein. Also included are the pharmaceutical compositions themselves.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The pharmaceutical compositions provided herein may be liquid, e.g. adapted for administration as a spray. Liquid preparations, such as those based on aqueous formulations, can include ancillary agents, for example a pH-buffering system (e.g., a buffer such as phosphate, borate, citrate or acetate buffers), a preservative, and/or an osmotic pressure controlling agent (e.g. glycerol or sodium chloride). For example, boric acid, sodium bicarbonate, sodium phosphate monobasic, sodium phosphate dibasic, and sodium phosphate dibasic heptahydrate can be used as buffering agents. In some embodiments, boric acid and sodium bicarbonate can be used together in a buffer system; sodium phosphate monobasic and sodium phosphate dibasic can be used together in a buffer system; and sodium phosphate dibasic heptahydrate can be used in a buffer system.

Suitable diluents include aqueous or non-aqueous diluents or combination thereof. Examples of aqueous diluents include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil-in-water emulsions or water-in-oil emulsions.

The pH of the compositions of the invention may be adjusted to the desired value using any suitable organic or inorganic acid or organic or inorganic base. Suitable organic acids include, but are not limited to, acetic acid, citric acid, glutamic acid and methane sulfonic acid. Suitable inorganic acids include, but are not limited to, hydrochloric acid and sulphuric acid. Suitable organic bases include, but are not limited to, meglumine, lysine and tromethamine (TRIS). Suitable inorganic bases include, but are not limited to, sodium hydroxide and potassium hydroxide.

In some embodiments, the liquid preparations have water as a diluent. Such preparations can be prepared by dispersing the conjugate and ancillary agents, the dispersion being conducted by any method usually employed for suspension or emulsification, e.g. ultrasonic treatment. Adjustment of the aqueous phase to neutrality (i.e. to pH in the range from about 6.5 to about 8) may be accomplished in any of the preparatory steps. In some cases, microemulsions can be prepared in which the size of the dispersed particles or droplets is of the order of 10 nm, thereby facilitating their passage across the nasal mucosa. Such microemulsions may be sterilized by filtration.

The term "pharmaceutically acceptable salt" refers to the relatively non-toxic, inorganic and organic acid addition salts of a conjugate provided herein. These salts can be prepared in situ during the final isolation and purification of a compound provided herein, or by separately reacting the conjugate in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, a conjugate provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a conjugate provided herein. These salts can likewise be prepared in situ during the final isolation and purification of the conjugate, or by separately reacting the purified conjugate in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Numerous delivery devices are available for intranasal administration such as instillation catheters, droppers, unit-dose containers, squeeze bottles pump sprays, airless and preservative-fee sprays, compressed air nebulizers, metered-dose inhalers, insufflators and pressurized metered dose inhalers. Devices vary in accuracy of delivery, dose reproducibility, cost, and ease of use. Currently, metered-dose systems provide the greatest dose accuracy and reproducibility. Suitable delivery devices for the conjugates provided herein will be clear to a person skilled in the art of pharmacology.

For example, for administration by inhalation, the conjugates can be delivered in the form of an aerosol spray from a pressured container or dispenser that contains a suitable propellant, e.g., a gas such as carbon dioxide, or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998) and U.S. Patent Publication Nos. 2008/0305077 and 2009/0047234, and International Patent Application No. WO 2008/049897. Liposomes (e.g., as described in U.S. Pat. No. 6,472,375), microencapsulation and nanoencapsulation can also be used. Biodegradable targetable microparticle delivery systems or biodegradable targetable nanoparticle delivery systems can also be used (e.g., as described in U.S. Pat. No. 6,471,996).

The determination of a therapeutically effective dosage of a conjugate provided herein will be based on animal model studies, followed up by human clinical trials, and is guided by determining therapeutically effective dosages and nasal administration protocols that significantly reduce the occurrence or severity of the targeted disease symptoms or conditions in the patient. Suitable models in this regard include, for example, murine, rat, porcine, feline, non-human primate, and other accepted animal model subjects known in the art. Ultimately, the dosage of conjugate provided herein will be at the discretion of the attendant, physician or clinician. The dosage can also be adjusted by the individual physician in the event of any complication.

EXAMPLES

The invention is further described in the following examples, which do not limit the scope of the invention described in the claims.

Example 1. Intranasal Delivery of a Guanidinoneomycin-Iduronidase Conjugate

Preclinical studies were conducted using the recombinant enzyme iduronidase. Before the enzyme was conjugated to guanidinoneomycin (GNeo), a type of guanidinoglycoside conjugation, the iduronidase (Aldurazyme) was treated with alkaline phosphatase to remove about 95% of mannose-6-phosphate (M6P) groups. The enzyme was incubated with GNeo-NHS (1:50) at 4° overnight. The conjugated enzymes were purified by heparin-Sepharose chromatography. Conjugation had almost no effect on enzyme specific activity: GNeo-AP-IDUA, 5 to 6 U/mg vs. IDUA: 6 to 7 Units/mg.

Intranasal administration of various forms of iduronidase to α-iduronidase-deficient mice (Idua$^{-/-}$; Homozygote) resulted in rapid uptake into the brain, as measured by enzyme activity in extracts prepared from the brain one hour after administration. Specifically, enzyme activity was measured following administration of wildtype (2 mg/kg, n=4), mutant (Idua$^{-/-}$; 2 mg/kg, n=4), IDUA-treated (2 mg/kg, n=4), AP-IDUA-treated (2 mg/kg, n=3), and GNeo-AP-IDUA treated Idua$^{-/-}$ mice (2 mg/kg; n=4). As shown in FIG. 1, the mice treated with the GNeo-AP-IDUA conjugate showed significantly more enzymatic activity. In contrast, unmodified iduronidase (i.e. enzyme that was not conjugated to guanidinoneomycin) was not taken up efficiently (IDUA, FIG. 1). The unmodified enzyme contains a glycan determinant (mannose-6-phosphate) that occurs naturally and that allows the enzyme to interact with mannose-6-phosphpate receptors on cells. The data indicates that using the targeting system facilitated by conjugation with a guanidinoaminoglycoside allows for efficient uptake of enzyme when administered intranasally. In addition, it was shown that simply modifying the enzyme with alkaline phosphatase does not appear to facilitate efficient transport into the brain (AP-IDUA, FIG. 1).

Example 2. Uptake of Enzyme into Different Parts of the Brain

Figure 2:
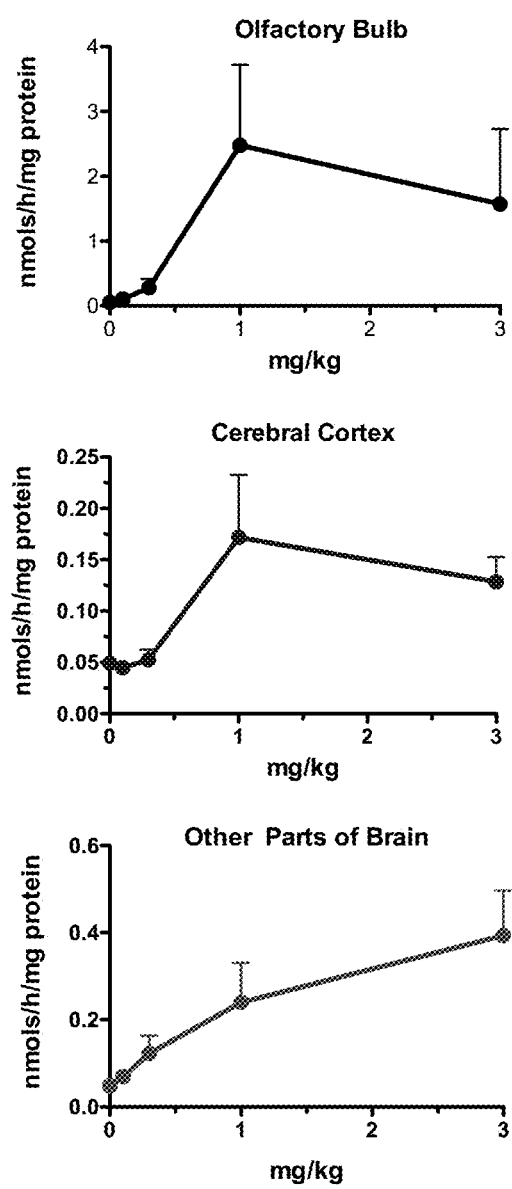
FIG. 2 is a series of line graphs showing uptake of the GNeo-AP-IDUA conjugate into various portions of the brain including the olfactory bulb and the cerebral cortex.

Each group of α-iduronidase-deficient mice (Idua$^{-/-}$; Homozygote, n=3) were administered 0, 0.1, 0.3 1, 3 mg/kg GNeo-AP-IDUA in PBS buffer intranasally. One hour following administration the mice were sacrificed and their brains were removed and dissected to isolate tissue from the olfactory bulb, the cerebral cortex, and "other parts of the brain." The total amount of tissue protein recovered from these various portions was ~1 mg, ~25 mg, and ~50 mg, respectively. The various tissues were then assayed for IDUA activity, which was expressed relative to the wet weight of each part of brain. As shown in FIG. 2, uptake into the olfactory bulb (OB) and cerebral cortex (CC) increased with concentration and saturated at ~1 mg/kg. Note that based on enzyme specific activity (nmols/hr/mg of tissue protein), enzyme concentration in the OB was much greater than in the CC, consistent with a mechanism in which enzyme was transported initially via a perineuronal/perivascular route to the OB. Enzyme uptake into the remainder of the brain, although lower in specific activity than in the OB, increased in proportion to administered enzyme concentration up to the highest concentration tested (3 mg/kg). It was calculated, based on total tissue protein, that the OB, CC and "Other parts of the Brain" accounted for ~13%, ~23%, and ~64% of the administered dose, demonstrating wide distribution of the enzyme.

Example 3. Reduction of Pathological Glycans by Intranasal Treatment

Figure 3:
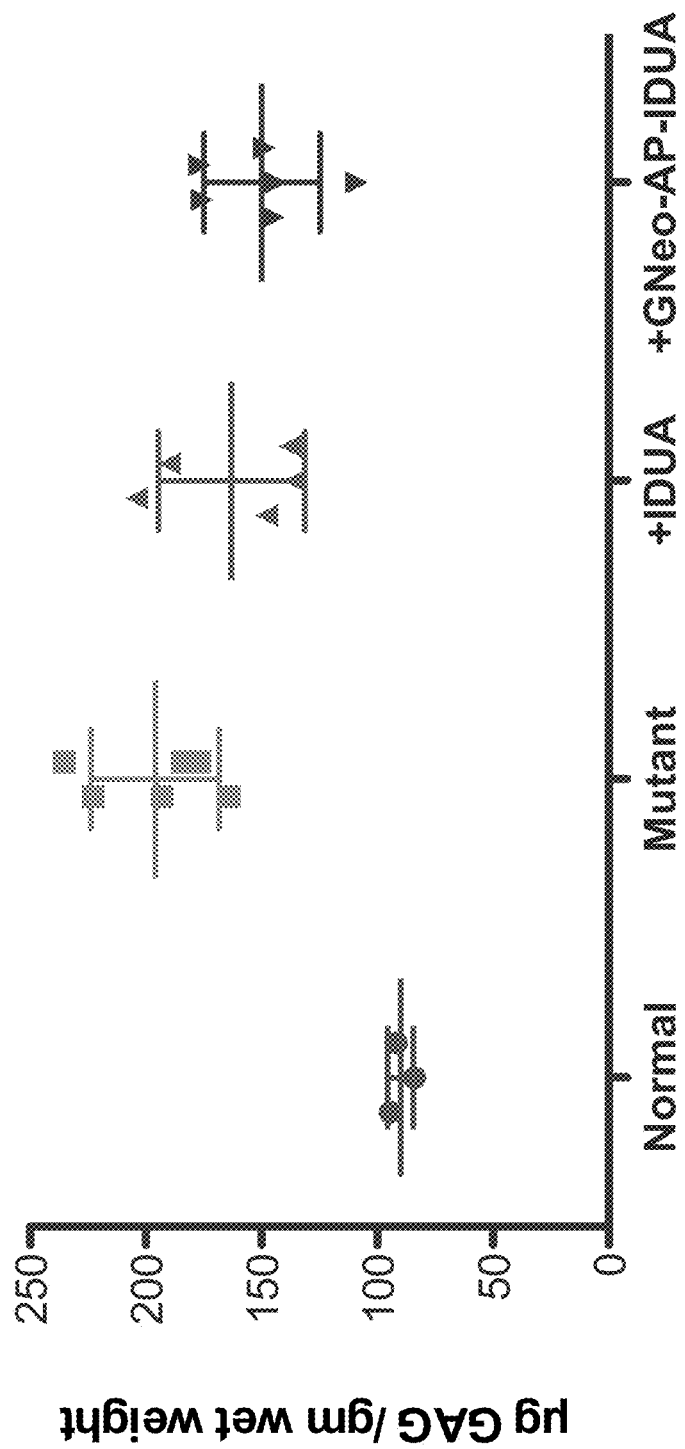
FIG. 3 illustrates a reduction of the amount of glycosaminoglycans in the brains of MPS I mice treated with and without 1 mg/kg IDUA or GNeo-AP-IDUA every other day for two weeks.

A mouse model of mucopolysaccharidosis (MPS) type I, which is null for the lysosomal enzyme, α-L-iduronidase (IDUA), was used to measure the amount of glycosaminoglycans in the brain following intranasal administration of 1 mg/kg IDUA or GNeo-AP-IDUA every other day for two weeks. Quantification of glycoaminoglycan was performed using the carbazole assay. The GNeo-conjugated enzyme significantly decreased the total GAG level in the mouse brain compared with the untreated mouse brains (FIG. 3). Data are represented as mean±SD (n=5 or 6). One-way analysis of variance (ANOVA) with Tukey's post-hoc analysis for comparison was applied for data analysis (*p<0.05).

Example 4. Intranasal Delivery of a Guanidinoneomycin-Sulfamidase Conjugate

Figure 4:
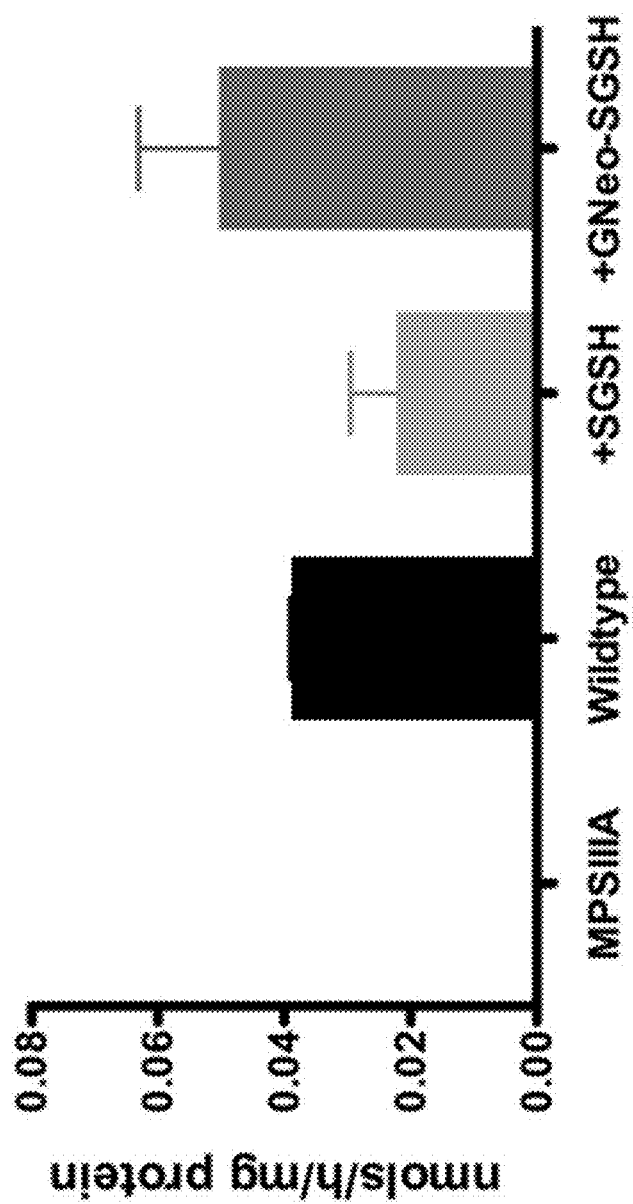
FIG. 4 is a bar graph illustrating the efficiency of delivery of sulfamidase (SGSH) in the brain of mice following intranasal administration of a GNeo-SGSH conjugate.

Sulfamidase (SGSH), which has mannose-6-phosphate terminated glycans, was conjugated to guanidinoneomycin (GNeo-SGSH). Intranasal administration of the 2 mg/kg conjugate to sulfamidase deficient mice (Sgsh$^{-/-}$) resulted in rapid uptake into the brain, as measured by enzyme activity in extracts prepared from the brain one hour after administration (+GNeo-SGSH, n=3 FIG. 4). The level of activity in the olfactory bulb of brain exceeded that found in wildtype animals (Wildtype, n=3 FIG. 4). In contrast, administration of 2 mg/kg of unmodified SGSH (i.e. enzyme that was not conjugated to guanidinoneomycin) was not taken up efficiently (+SGSH, FIG. 4). The data indicates that using the targeting system facilitated by conjugation with a guanidinoglycoside allows for efficient delivery of enzyme into brain when administered intranasally.

Example 5. Antibody Delivery to the Brain

Figure 5:
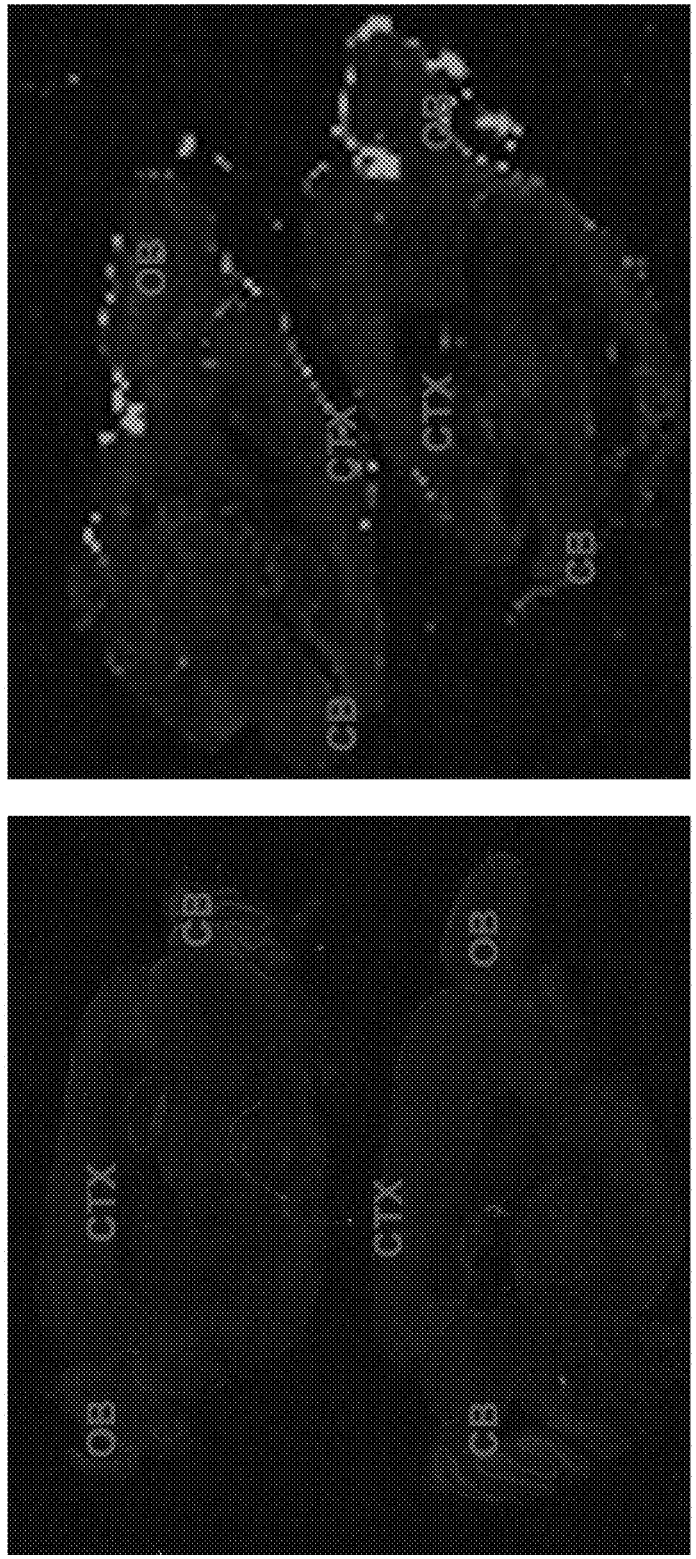
FIG. 5 is a photographic image of a brain section of mice intranasally administered a Goat Chicken IgG (IgY) (H+L) conjugated with Dylight 800 and modified with GNeo (0.5 mg/kg). The image on the left is a section from an animal treated with IgY-Dylight 800. The image on the right is a similar section from an animal treated with the GNeo-IgY-Dylight800 conjugate.

Chicken IgG (IgY) (H+L chains) was incubated with GNeo-NHS (1:50) at 4° overnight. The conjugated antibodies were purified by heparin-Sepharose chromatography. and administered intranasally to mice (0.5 mg/kg, n=2 per each group). After 1 hour, the mouse was anesthetized and perfused with 4% PFA (paraformaldehyde) in buffer. The brain was excised and post-fixed in 4% PFA for 2 hours. The tissue was permeated with 30% sucrose for 24 hours, sectioned sagitally (20 microns), and imaged (LI-COR Odyssey) (FIG. 5). The image on the left is a section from an animal treated with IgY-Dylight 800 as a control, while the image on the right shows a similar section from an animal treated with GNeo-IgY-Dylight800. This data shows that the targeting system facilitated by conjugation with a guanidiniaminoglycoside allows for efficient delivery of antibodies into brain when administered intranasally.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a lysosomal storage disease affecting the brain of a patient in need thereof, the method comprising intranasally administering to the patient a therapeutically effective amount of a conjugate comprising one or more guanidinoglycosides and an enzyme, wherein the enzyme is useful for treating the lysosomal storage disease of the patient.

2. The method of claim 1, wherein the guanidinoglycoside is covalently bound to the enzyme, wherein the covalent bond is direct or optionally through a linker.

3. The method of claim 2, wherein the linker comprises one or more of a hydrocarbon moiety, a polyethylene glycol (PEG) moiety, an oligoamide moiety, an oligoester, and functionalized and/or chemically and enzymatically cleavable moieties.

4. The method of claim 1, wherein the enzyme is selected from the group consisting of: α-D-mannosidase; N-aspartyl-β-glucosaminidase; acid lipase; hexosaminidase A; α-galactosidase A; β-galactosidase; ceramidase; fucosidase; β-glucosidase; N-acetylglucosamine-1-phosphotransferase; galactocerebrosidase; arylsulfatase A; N-acetylglucosamine-1-phosphotransferase; α-L-iduronidase; iduronate sulfatase; heparan sulfamidase; N-acetylglucosaminidase; acetyl-CoA:α-glucosaminide acetyltransferase; N-acetylglucosamine 6-sulfatase; N-acetylgalactosamine-6-sulfate sulfatase; N-acetylgalactosamine-4-sulfatase; β-glucuronidase; hyaluronidase; sialidase; sulfatase; sphingomyelinase; acid α-glucosidase; β-mannosidase; cathepsin K; β-hexosaminidase A; β-hexosaminidase B; α-N-acetylgalactosaminidase; sialin; and hexosaminidase A.

5. The method of claim 4, wherein the enzyme is β-glucosidase or α-iduronidase.

6. The method of claim 1, wherein the lysosomal storage disease is selected from the group consisting of: Activator Deficiency; Alpha-mannosidosis; Aspartylglucosaminuria; Cholesteryl ester storage disease; Chronic Hexosaminidase A Deficiency; Cystinosis; Danon disease; Fabry disease; Farber disease; Fucosidosis; Galactosialidosis; Gaucher disease; GM1 gangliosidosis; I-Cell disease; Infantile Free Sialic Acid Storage Disease; Juvenile Hexosaminidase A deficiency; Krabbe disease; Metachromatic Leukodystrophy; Mucopolysaccharidoses disorders; Multiple sulfatase deficiency; Niemann-Pick disease; Neuronal Ceroid Lipofuscinoses; Pompe disease; Pycnodysostosis; Sandhoff disease; Schindler disease; Salla disease; Tay-Sachs; and Wolman disease.

7. The method of claim 6, wherein the Mucopolysaccharidoses disorders are selected from the group consisting of: Pseudo-Hurler polydystrophy; Hurler Syndrome; Scheie syndrome; Hurler-Scheie syndrome; Hunter syndrome; Sanfilippo syndrome type A; Sanfilippo syndrome type B; Sanfilippo syndrome type C; Sanfilippo syndrome type D; Morquio type A; Morquio type B; Maroteaux-Lamy; Sly syndrome; and Natowicz syndrome Hyaluronidase deficiency.

8. The method of claim 7, wherein the Neuronal Ceroid Lipofuscinoses are selected from the group consisting of: CLN6 disease; Batten-Spielmeyer-Vogt/Juvenile NCL/CLN3 disease; Finnish Variant/Late Infantile CLN5; Jansky-Bielschowsky disease/Late infantile CLN2/TPP1 Disease; Kufs/Adult-onset NCL/CLN4 disease; Northern Epilepsy/variant Late Infantile CLN8; Santavuori-Haltia/Infantile CLN1/PPT disease; and β-mannosidosis.

9. The method of claim 1, wherein the guanidinoglycoside comprises an aminoglycoside antibiotic.

10. The method of claim 1, wherein the guanidinoglycoside is selected from the group consisting of guanidino-amikacin, guanidino-gentamicin, guanidino-kanamycin, guanidino-neomycin, guanidino-netilmicin, guanidino-O-2, 6-diamino-2,6-dideoxy-beta-L-idopyranosyl (1→3)-O-beta-D-ribofuranosyl (1→5)-O-[2-amino-2-deoxy-alpha-D-glucopyranosyl (1→4)]-2-deoxystreptamine, guanidino-paramycin, guanidino-streptomycin, guanidino-paromomycin, guanidine-dibekacin, guanidine-arbekacin, guanidino-isepamicin, guanidino-sisomicin, guanidine-ribostamycin, and guanidino-tobramycin.

11. The method of claim 1, wherein the enzyme has a molecular weight of greater than 27,500 Daltons.

12. A method for increasing the cellular uptake of an enzyme useful for treating a lysosomal storage disease in a patient, the method comprising:
    a) coupling the enzyme to one or more guanidinoglycosides to form a conjugate; and
    b) administering a therapeutically effective amount of the conjugate to the brain of the patient via intranasal administration.

13. The method of claim 12, wherein the enzyme has a molecular weight of greater than 27,500 Daltons.

14. A method for treating a CNS disorder in a patient, the method comprising administering to the brain of the patient via intranasal administration a therapeutically effective amount of a conjugate comprising one or more guanidinoglycosides and a therapeutically active compound or polypeptide useful for treating the CNS disorder.

15. The method of claim 14, wherein the therapeutically active compound or polypeptide has a molecular weight of greater than 27,500 Daltons.

* * * * *

UNITED STATES PATENT AND TRADEMARK OFFICE
CERTIFICATE OF CORRECTION

PATENT NO. : 9,757,468 B2
APPLICATION NO. : 14/774257
DATED : September 12, 2017
INVENTOR(S) : Jeffrey D. Esko, Yitzhak Tor and Wenyong Tong It is certified that error appears in the above-identified patent and that said Letters Patent is hereby corrected as shown below:

In the Specification

Column 1, Line 11, please delete "No." and insert -- Nos. --, therefor;

Column 1, Line 19, please delete "Grant Nos. GM077471 and GM33063" and insert -- Grant No. NS065768, --, therefor.

Signed and Sealed this
Sixth Day of March, 2018

Andrei Iancu
*Director of the United States Patent and Trademark Office*